United States Patent [19]

Huff et al.

[11] Patent Number: 4,506,074
[45] Date of Patent: Mar. 19, 1985

[54] 2-[2-PYRIDINYLOXY(THIO OR AMINO)METHYL]-1H-IMIDAZOLES AND DERIVATIVES

[75] Inventors: Joel R. Huff, Lederach; Walfred S. Saari, Lansdale; John J. Baldwin, Gwynedd Valley, all of Pa.

[73] Assignee: Merck & Co., Inc., Rahway, N.J.

[21] Appl. No.: 439,697

[22] Filed: Nov. 8, 1982

[51] Int. Cl.³ .......................................... C07D 401/12
[52] U.S. Cl. .................................................. 546/278
[58] Field of Search ....................................... 546/278

[56] References Cited

U.S. PATENT DOCUMENTS

| | | | |
|---|---|---|---|
| 3,907,816 | 9/1975 | Winkelmann et al. | 546/278 |
| 4,046,896 | 9/1977 | Winkelmann et al. | 546/278 |
| 4,078,063 | 3/1978 | Lumma et al. | 424/250 |
| 4,376,772 | 3/1983 | Saari et al. | 424/250 |
| 4,381,302 | 4/1983 | Huff et al. | 424/250 |
| 4,442,103 | 4/1984 | Saari | 424/250 |
| 4,456,604 | 6/1984 | Saari | 424/250 |

OTHER PUBLICATIONS

Ser. No. 439,698, by Huff et al.
Ser. No. 436,753, by Saari.

*Primary Examiner*—Jane T. Fan
*Attorney, Agent, or Firm*—William H. Nicholson

[57] ABSTRACT

2-[2-Pyridinyloxy(thio or amino)methyl]-1H-imidazoles and derivatives and acid addition salts thereof generally are selective $\alpha_2$-adrenergic receptor antagonists and $\alpha_1$-adrenergic receptor agonists and thereby useful as antidepressants and nasal decongestants.

3 Claims, No Drawings

2-[2-PYRIDINYLOXY(THIO OR AMINO)METHYL]-1H-IMIDAZOLES AND DERIVATIVES

BACKGROUND OF THE INVENTION

This invention is concerned with novel 2-[2-pyridinyloxy(thio or amino)methyl]-1H-imidazoles and derivatives or pharmaceutically acceptable salts thereof of structural Formula I

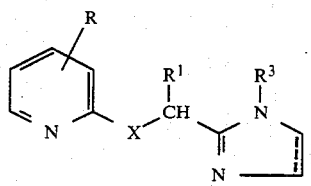

which have antidepressant, nasal decongestant and antihypertensive activity. It also relates to a process for preparing the novel compounds, pharmaceutical compositions comprising the novel compounds and to a method of treating depression, and nasal congestion with the novel compounds.

The pyridine group is common among compounds with useful pharmacological properties, such as the 2-piperazinyl-5 (and/or 6)-substituted pyridines of U.S. Pat. No. 4,078,063 which are anorexigenic agents and also said to have antidepressant activity by virtue of their pharmacological influence on serotonin levels.

Now, with the present invention there is provided a group of substituted pyridines of structural Formula I which generally are antidepressants and nasal decongestants by virtue of their ability to selectively antagonize $\alpha_2$-adrenergic receptor sites, and to stimulate $\alpha_1$-adrenergic receptors.

The concept that the complex clinical state of depression is linked to a functional deficiency of monoamines in the central nervous system is now widely accepted. Numerous biochemical and clinical observations support the proposal that many forms of depressive illness are associated with reductions in adrenergic activity of functionally important sites in the brain. Thus, classical antidepressive drugs, such as amitriptyline and imipramine, are believed to act by blocking the neuronal reuptake of norepinephrine and/or serotonin, thereby enhancing the availability of the monoamines as neurotransmitters.

Combinations of norepinephorine reuptake blockers or monoamine oxidase inhibitors with selective $\alpha_2$-adrenergic receptor antagonists, their effects being at least additive, form another aspect of this invention.

In addition of $\alpha_1$-adrenergic receptors which mediate postsynaptic responses to the neurotransmitter norepinephrine, other adrenergic receptors are present at or near sympathetic terminals. These latter receptors, $\alpha_2$-adrenergic receptors, form part of a negative feedback system which modulates noradrenergic neurotransmission by controlling the impulse-induced release of norepinephrine from presynaptic terminals. Activation of $\alpha_2$-adrenergic receptors results in a decrease in the amount of norepinephrine normally released from the nerve terminals by nerve impulses while antagonism of $\alpha_2$-adrenergic receptors increases norepinephrine release. Therefore, molecules that block $\alpha_2$-adrenergic receptors afford an alternate approach to enhancement of noradrenergic function and the treatment of depression associated with an absolute or relative deficiency of adrenergic function.

Mianserin, a clinically effective antidepressant which has been reported to have minimal in vivo norepinephrine reuptake inhibiting properties, blocks $\alpha_2$-adrenergic receptors. However, mianserin fails to exhibit any important selectivity for $\alpha_1$- or $\alpha_2$-adrenergic receptors suggesting that mianserin, in vivo, blocks $\alpha_1$-receptors at about the same dose required to block $\alpha_2$-receptors (Clineschmidt et al., *Arch. Int. Pharmacodyn. Ther.*, 242, 59 (1979)).

The compounds of the present invention having $\alpha_2$ properties reduce blood pressure by virtue of their ability to stimulate central adrenergic receptorsites.

The compounds of the present invention, being highly selective $\alpha_2$-adrenergic receptor antagonists, have definite therapeutic advantages over the more non-selective $\alpha_1$-, $\alpha_2$-antagonists. Since $\alpha_1$-(or postsynaptic) blockade opposes the increase in nor-adrenergic transmission initiated through $\alpha_2$-blockade, compounds that selectively antagonize $\alpha_2$-adrenergic receptors induce enhanced neurotransmission at noradrenergic synapses. In addition, molecules with reduced $\alpha_1$-adrenergic receptor blocking properties, or with $\alpha_1$-adrenergic agonist properties such as the compounds of the present invention, produce less orthostatic hypotension, an undesirable side-effect (Synder, Pharmakopsychiat, 13, 62 (1980)).

Compounds with $\alpha_1$-adrenergic agonist properties generally cause marked vasoconstriction and blanching when applied to nasal and pharyngeal mucosal surfaces. This ability to shrink the nasal mucosa makes such compounds useful in the treatment of mucosal congestion accompanying hay fever, allergic rhinitis, sinusitus and other congestive respiratory conditions.

The compounds of the present invention in addition to being $\alpha_1$-adrenergic agonists are also $\alpha_2$-adrenergic antagonists. The ability to block presynaptic $\alpha_2$-adrenergic receptors increases norepinephrine release which augments the shrinking of the nasal mucosa caused by the postsynaptic $\alpha_1$-adrenergic stimulation.

As stated previously the novel compounds of formula I generally are $\alpha_2$-antagonists/$\alpha_1$-agonists thereby manifesting antidepressant and nasal decongestant properties.

DETAILED DESCRIPTION OF THE INVENTION

This invention is concerned with compounds of structural formula I:

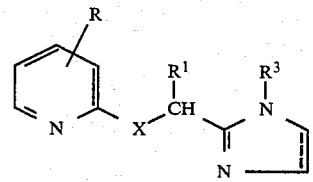

or a pharmaceutically acceptable salt thereof, wherein:
R is
(1) hydrogen;
(2) halo such as fluoro, chloro, bromo or iodo, especially fluoro or chloro;
(3) $C_{1-3}$ alkyl, such as methyl, ethyl or propyl;
(4) hydroxy;

(5) $C_{1-3}$ alkoxy, such as methoxy, ethoxy or propoxy;
(6) phenyl-$C_{1-3}$ alkoxy, especially benzyloxy;
(7) $C_{3-5}$ alkenyloxy, especially allyloxy;
(8) di($C_{1-3}$ alkyl)amino, especially dimethylamino;
(9) nitro;
(10) trifluoromethyl;
(11) sulfonamido;
(12) N,N-di($C_{1-3}$alkyl)sulfonamido; and
(13) $C_{2-5}$alkanoyl, especially acetyl;

X is

—S—, >SO, >SO$_2$, or —O—; and $R^1$, $R^2$ and $R^3$ are independently hydrogen or $C_{1-3}$ alkyl;
and the dotted line in the imidazole ring is an optional double bond.

It is preferred that R be hydrogen chloro or methoxy. It is further preferred that X be —S—, —O— or —NH—.

The pharmaceutically acceptable salts coming within the purview of this invention include the pharmaceutically acceptable acid-addition salts. Acids useful for preparing these acid-addition salts include inter alia, inorganic acids, such as the hydrohalic acids (e.g., hydrochloric and hydrobromic acid), sulfuric acid, nitric acid, and phosphoric acid, and organic acids such as maleic, fumaric tartaric, citric, acetic, benzoic, 2-acetoxybenzoic, salicylic, succinic acid, theophylline, 8-chlorotheophylline, p-aminobenzoic, p-acetamidobenzoic, methanesulfonic, or ethane disulfonic.

The novel compounds of this invention are prepared in accordance with the following general Reaction Scheme I:

Reaction Scheme I:

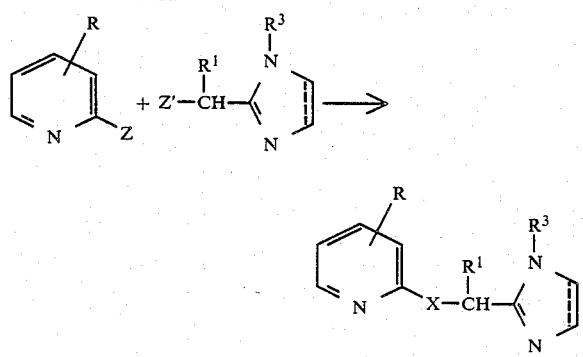

wherein Z and Z' are XH and Y respectively or Z and Z' and Y and XH respectively.

More specifically, the process is represented by Reaction Scheme Ia or Ib.

Reaction Scheme Ia:

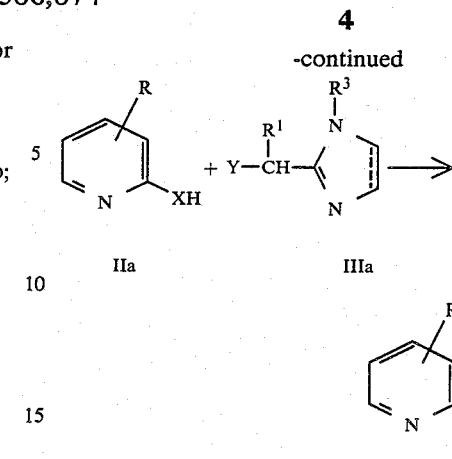

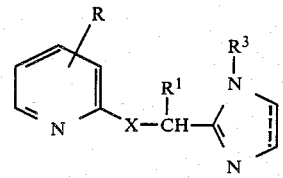

Reaction Scheme Ib:

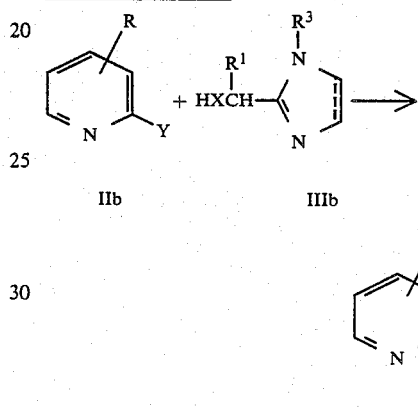

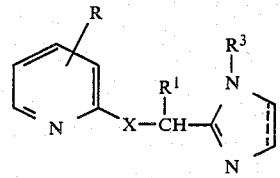

wherein R, $R^1$ and $R^3$ are as previously defined, X is

—S—, or —O—, and Y is halogen, especially chloro, $C_{1-5}$alkylsulfonyloxy, such as methanesulfonyloxy; or benzenoid arylsulfonyloxy such as, benzenesulfonyloxy or toluenesulfonyloxy.

The reaction is conducted in an inert organic solvent such as a $C_{1-4}$alkanol, preferably methanol, or acetonitrile, dimethylformamide, dimethylsulfoxide or hexamethylphosphoramide, in the presence of a strong base such as an alkali metal hydride or alkali metal $C_{1-4}$ alkoxide, for example sodium hydride or potassium tert-butoxide.

There are employed temperatures ranging from about 15° C. to about 100° C., preferably under anhydrous conditions until a substantial amount of desired compound of Formula I is obtained, typically for a period of from about 2 to about 24 hours, preferably from about 3 to 20 hours.

The compounds in which X is SO or SO$_2$ are prepared by treating the corresponding sulfide with a peracid in a strongly acidic medium, such as peroxytrifluoroacetic acid in trifluoroacetic acid medium at about −10° C. to about +10° C.

In the novel method of selectively antagonizing α$_2$-adrenergic receptors in a patient for the purpose of treating depression, a novel compound or pharmaceutically acceptable salt thereof, is administered in an amount ranging from about 0.01 to about 20 mg per kg of body weight per day, preferably from about 0.1 to about 10 mg per kg of body weight per day in a single dose or in 2 to 4 divided doses.

If used in combination with a norepinephrine reuptake blocker, or a monoamine oxidase inhibitor, type of antidepressant, the dose of each is about half the recommended dose.

For the treatment of nasal congestion there is used a 0.01–1% aqueous solution of a soluble salt which is administered at 2–5 drops per dose up to 3 to 4 times per day.

The compounds, or pharmaceutically acceptable salts thereof, of the present invention, in the described dosages, are administered orally, intraperitoneally, subcutaneously, intramuscularly, intravenously or as nose drops. They are preferably administered orally for the treatment of depression, for example in the form of tablets, troches, capsules, elixirs, suspensions, syrups, wafers, chewing gum, or the like prepared by art recognized procedures. The amount of active compound in such therapeutically useful compositions or preparations is such that a suitable dosage will be obtained.

The following examples illustrate the present invention without, however, limiting the same thereto.

EXAMPLE 1

2-[3-Chloro-2-pyridinyloxymethyl]-4,5-dihydro-1H-imidazole Hydrochloride

2-Hydroxymethyl-4,5-dihydro-1H-imidazole hydrochloride (1.98 g, 14.5 mmol) was added to a stirred slurry of sodium hydride (1.49 g of a 50% dispersion in mineral oil, 31 mmol, previously washed with pentane and dried under nitrogen) and dimethylformamide, 70 ml. After 15 minutes, a solution of 2,3-dichloropyridine (2.22 g, 15 mmol) in 10 ml of dimethylformamide was added and stirring continued for 3 hours. The reaction mixture was then poured into 150 ml of water, and extracted with three 90 ml portions of ethyl acetate. The ethyl acetate extracts were combined, dried over anhydrous magnesium sulfate, filtered and concentrated to an oil which was purified by flash chromatography over silica gel 60 (230–400 mesh) by elution with 10% methanol-90% chloroform saturated with ammonia. The purified base was dissolved in ethanol, treated with an ethanolic-hydrogen chloride solution and the monohydrochloride salt, m.p. 194°–196° C. (dec.) precipitated with diethyl ether.

Employing the procedure substantially as described in Example 1, but substituting for the 2,3-dichloropyridine and the 2-hydroxymethyl-4,5-dihydroimidazole used therein, equimolecular amounts of 2-chloro-3-R-pyridine and 2-hydroxy(R¹)methyl-4,5-dihydro-1H-imidazole respectively, there are produced the 2-[3-R-2-pyridinyloxy(R¹)methyl]-4,5-dihydro-1H-imidazoles described in Table I:

TABLE I

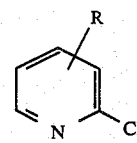

| R | R¹ | |
|---|---|---|
| H | H | |
| 3-F | H | |
| 3-F | —CH₃ | |
| 3-Br | H | |
| 3-OCH₃ | H | (m.p. 210-211° as HCl salt) |
| 3-OCH₂C₆H₅ | H | |
| 3-CH₃ | H | |
| 3-OCH₂—CH=CH₂ | H | |
| 5-NO₂ | H | |
| 5-N(CH₃)₂ | H | |
| 3-CF₃ | H | |
| 3-SO₂NH₂ | H | |
| 3-SO₂N(CH₃)₂ | H | |
| 5-COC₂H₅ | H | |

EXAMPLE 2

2-[2-Pyridinylthiomethyl]-4,5-dihydro-1H-imidazole Dihydrochloride

To a solution of sodium hydride (1.1 g of a 50% dispersion in mineral oil, 23 mmol) in 50 ml of methanol was added 2-thiopyridone (1.2 g, 11 mmol) followed by 2-chloromethyl-4,5-dihydro-1H-imidazole hydrochloride (1.7 g, 11 mmol). After stirring at 20°–25° C. for 18 hours, the reaction mixture was poured into 100 ml of a 5% sodium hydroxide solution and the product extracted into chloroform, (3×50 ml). The chloroform extracts were combined, dried over anhydrous sodium sulfate, filtered and concentrated to an oil which after triturating with hot hexane slowly crystallized. The product was dissolved in ethanol, treated with excess ethanolic-hydrogen-chloride and the dihydrochloride salt, m.p. 188°–190° C. precipatated with diethyl ether.

Employing the procedure substantially as described in Example 2, but substituting for the 2-thiopyridone and the 2-chloromethyl-4,5-dihydro-1H-imidazole used therein, equimolecular amounts of 3-R-2-thiopyridone and 2-chloro-(R¹)-methyl-4,5-dihydro-1H-imidazole respectively, there are produced the 2-[3-R-2-pyridinylthio(R¹)methyl]-4,5-dihydro-1H-imidazoles described in Table II:

TABLE II

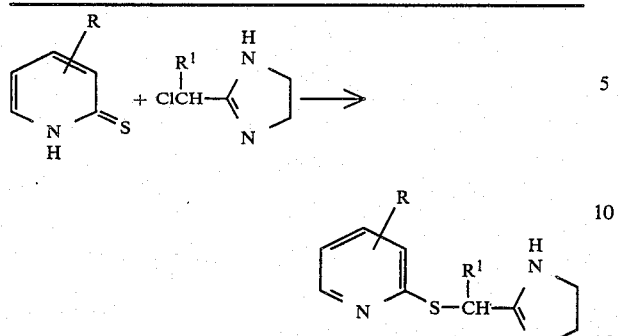

| R | R¹ | |
|---|---|---|
| 3-Cl | H | (m.p. 93–94° C. as the hydrogen maleate) |
| 3-F | H | |
| 3-F | —CH₃ | |
| 3-Br | H | |
| H | —C₂H₅ | |
| 3-Cl | —C₃H₇—n | |

EXAMPLE 3

2-[3-Chloro-2-pyridinylaminomethyl]-4,5-dihydro-1H-imidazole Hydrogen Maleate 2-Amino-3-chloropyridine (2.6 g, 20 mmol) was added in portions to a stirred slurry of sodium hydride (1.9 g of a 50% dispersion in mineral oil, 40 mmol) in 50 ml of dimethylformamide. After stirring at 20°–25° C. for 1 hour and 65° C. for 1 hour, 2-chloromethyl-4,5-dihydro-1H-imidazole hydrochloride (3.1 g, 20 mmol) was added portionwise. The reaction mixture was stirred at 65° C. for 20 hours and then most of the dimethylformamide was removed under reduced pressure. The residue was mixed with 50 ml of water, acidified by the addition of concentrated hydrochloric acid and extracted with diethyl ether to remove nonbasic material. The aqueous extract was made basic with a 40% sodium hydroxide solution and the product extracted into diethyl ether. After washing the ether extract with a saturated sodium chloride solution, the ether layer was dried over anhydrous sodium sulfate, filtered and concentrated. This crude product was purified further by flash chromatography over silica gel 60 (230–400 mesh) and elution with 1% methanol-99% chloroform saturated with ammonia. The product was dissolved in ethanol, treated with an equivalent of maleic acid, and the hydrogen maleate salt of 2-[3-chloro-2-pyridinylaminomethyl]-4,5-dihydro-1H-imidazole, m.p. 153°–156° C. was precipitated with ethyl acetate.

Employing the procedure substantially as described in Example 3, but substituting for the 2-amino-3-chloropyridine and the 2-chloromethyl-4,5-dihydro-1H-imidazole used therein, equimolecular amounts of 2-(R² amino)-3-R-pyridine and 2-chloro(R¹)methyl-4,5-dihydro-1H-imidazole, respectively, there are produced the 2-[3-R-2-pyridinyl-N-R²-amino(R¹)methyl]-4,5-dihydro-1H-imidazoles described in Table III.

TABLE III

| R | R¹ | R² |
|---|---|---|
| H | H | H |
| 3-F | H | H |
| 5-F | —CH₃ | H |
| 3-Br | H | H |
| 3-F | H | —CH₃ |
| 3-Cl | —C₂H₅ | H |
| H | H | —C₂H₅ |
| H | H | —C₃H₇-n |
| 5-CH₃ | H | CH₃ (m.p. 138.5–139.5° C. as the hydrogen maleate) |

EXAMPLE 4

2-(3-Chloro-2-pyridinylthiomethyl)-1H-imidazole hydrogen maleate

To a solution of 2.20 g (20.0 mmol) of triethylamine in 30 ml of ethanol was added 0.56 g (10.0 mmol) of 3-chloro-2-mercaptopyridine. After 30 minutes at room temperature, 0.770 g (10 mmol) of 2-(chloromethyl)-1H-imidazole hydrochloride was added, and the reaction was stirred at room temperature overnight. The reaction was then concentrated and diluted with 30 ml of 5% NaOH. The mixture was extracted with 2×30 ml of chloroform. The combined extracts were dried (Na₂SO₄), filtered, and concentrated to an oil which was purified by flash chromatography (230–400 mesh SiO₂, 5% MeOH/CHCl₃ saturated with NH₃ as eluent). The product is mixed with maleic acid in acetone and ether to afford its hydrogen maleate salt. m.p. 118°–120° C.

Employing the procedure substantially as described in Example 4, but substituting for the 3-chloro-2-mercapto-pyridine and the 2-chloromethyl-1H-imidazole used therein, equimolecular amounts of 3-R-2-thiopyridone and 2-chloro(R¹)methyl-1H-imidazole respectively, there are produced the 2-[3-R-2-pyridinylthio-(R¹)methyl]-1H-imidazoles described in Table IV:

TABLE IV

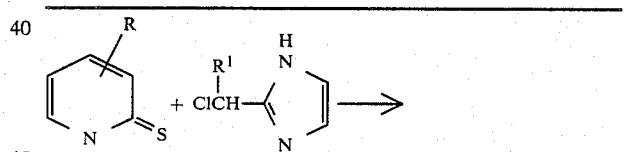

| R | R¹ |
|---|---|
| H | H |
| 3-F | H |
| 3-F | —CH₃ |
| 3-Br | H |
| H | —C₂H₅ |
| 3-Cl | —C₃H₇—n |

EXAMPLE 5

2-(3-chloro-2-pyridinylthiomethyl)-1-methyl-1H-imidazole hydrogen maleate

A solution of sodium ethoxide in ethanol was prepared by the addition of 460 mg (20 mmol) of sodium metal to 30 ml of ethanol. To this was added 1.13 g (10 mmol) of 3-chloro-2-mercapto-pyridine and 1.66 g (10 mmol) of 2-chloromethyl-1-methylimidazole hydrochloride. After 18 hours at room temperature, the reaction was concentrated to dryness and dissolved in 50 ml of 5% NaOH. The aqueous solution was extracted with 2×40 ml chloroform, and the combined organic extracts were dried ($Na_2SO_4$), filtered, and concentrated to afford an oil. The crude product was purified by flash chromatography (5% $MeOH/CHCl_3$ saturated with $NH_3$ as eluent, 230–400 mesh $SiO_2$) to give the product, which was mixed with maleic acid in acetone and ether, affording the hydrogen maleate salt m.p. 115°–117° C.

Employing the procedure substantially as described in Example 5, but substituting for the 3-chloro-2-thiopyridone and the 2-chloromethyl-1H-1-methyl imidazole used therein, equimolecular amounts of 3-R-2-thiopyridone and 2-chloro-($R^1$)methyl-1H-1-$R^3$-imidazole respectively, there are produced the 2-[3-R-2-pyridinylthio-($R^1$)methyl]-1H-1-$R^3$-imidazoles described in Table V:

TABLE V

| R | $R^1$ | $R^3$ |
|---|---|---|
| H | H | $-CH_3$ |
| 3-F | H | $-CH_5$ |
| 3-F | $-CH_3$ | $-CH_3$ |
| 3-Br | H | $-C_2H_5$ |
| H | $-C_2H_5$ | $-CH_3$ |
| 3-Cl | $-C_3H_7-n$ | $-CH_3$ |

EXAMPLE 6

2-(3-Chloro-2-pyridinylsulfinylmethyl)-1H-imidazole, hydrogen oxalate

In a 25 ml, three necked, round-bottomed flask, outfitted with a magnetic stirrer, thermometer, and addition funnel, is placed trifluoroacetic acid (5 ml) and 2-(3-chloro-2-pyridylthiomethyl)-1H-imidazole (1.5 g; 6.6 mmol). Peroxytrifluoroacetic acid (1.65 ml; 6.6 mmol), from a stock solution prepared by mixing 8.6 ml of 30% hydrogen peroxide and trifluoroacetic acid to a final volume of 25 ml to give 4M solution of the peracid, is added dropwise to the stirred, cooled (0°) sulfide mixture. The reaction is kept at 0° until the peroxide is discharged (starch-iodide paper) and the starting material is consumed. Solvent is removed in vacuo and the residue dissolved in methylene chloride, washed with 5% sodium hydroxide, and dried ($Na_2SO_4$). Removal of the solvent affords the sulfoxide which was crystallized as its hydrogen oxalate salt.

EXAMPLE 7

2-(3-Chloro-2-pyridylsulfonylmethyl)-1H-imidazole hydrogen oxalate

This compound is prepared by following the procedure of Example 6 employing 2.0 equivalents of peroxytrifluoroacetic acid.

EXAMPLE 8

| Pharmaceutical Formulation | Mg/Capsule |
|---|---|
| Active Ingredient | 6 |
| Starch | 87 |
| Magnesium stearate | 7 |

The active ingredient, starch and magnesium stearate are blended together. The mixture is used to fill hard shall capsules of a suitable size at a fill weight of 100 mg per capsule.

EXAMPLE 9

Pharmaceutical Formulation—including a norepinephrine reuptake blocker

| Ingredients | Mg/capsule |
|---|---|
| Active ingredient | 3 |
| Amitriptyline hydrochloride | 15 |
| Starch | 75 |
| Magnesium stearate | 7 |

The active ingredients, starch and magnesium stearate are blended together. The mixture is used to fill hard shell capsules of a suitable size at a fill weight of 100 mg per capsule.

EXAMPLE 10

Pharmaceutical Formulation for nose drops

| Ingredients | |
|---|---|
| Active Ingredient | 0.25 mg |
| Aminoacetic acid | 3.8 mg |
| Sorbitol solution, U.S.P. | 57.1 mg |
| Phenylmercuric acetate | 0.02 mg |
| Benzalkonium chloride | 0.2 mg |
| Hydrochloric acid to pH 4.5–5.0 | |
| Water, q.s. 1 ml. | |

What is claimed is:
1. The compound of structural Formula I:

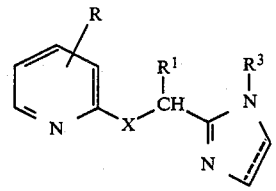

or a pharmaceutically acceptable salt thereof, wherein:
R is
 (1) hydrogen;
 (2) halo;
 (3) $C_{1-3}$ alkyl;
 (4) hydroxy;
 (5) $C_{1-3}$ alkoxy;
 (6) phenyl-$C_{1-3}$ alkoxy;

(7) C$_{3-5}$ alkenyloxy;
(8) di(C$_{1-3}$ alkyl)amino;
(9) nitro;
(10) trifluoromethyl;
(11) sulfonamido;
(12) N,N-di(C$_{1-3}$alkyl)sulfonamido; and
(13) C$_{2-5}$alkanoyl;

X is

—S—, —SO, —SO$_2$, or —O—; and
R$^1$, R$^2$ and R$^3$ are independently hydrogen or C$_{1-3}$ alkyl;
and the dotted line is an optional double bond.

2. The compound of claim 1 wherein R is hydrogen, chloro or methoxy; and X is —S—, —O— or —NH— or a pharmaceutically acceptable salt thereof.

3. The compound of claim 2 which is 2-[3-chloro-2-pyridinylthiomethyl]-4,5-dihydro-1H-imidazole; 2-[3-chloro-2-pyridinylaminomethyl[-4,5-dihydro-1H-imidazole; or 2-[3-methoxy-2-pyridinyloxymethyl]-4,5-dihydro-1H-imidazole; or a pharmaceutically acceptable salt thereof.

* * * * *